United States Patent
Takacs

(10) Patent No.: US 10,947,603 B2
(45) Date of Patent: Mar. 16, 2021

(54) HPV DETECTION METHOD

(71) Applicant: CELLCALL KFT., Budapest (HU)

(72) Inventor: Tibor Takacs, Pilisjaszfalu (HU)

(73) Assignee: CellCall KFT., Budapest (HU)

( * ) Notice: Subject to any disclaimer, the term of this patent is extended or adjusted under 35 U.S.C. 154(b) by 0 days.

(21) Appl. No.: 15/739,385

(22) PCT Filed: Jun. 30, 2016

(86) PCT No.: PCT/EP2016/065265
§ 371 (c)(1),
(2) Date: Jan. 14, 2020

(87) PCT Pub. No.: WO2017/001544
PCT Pub. Date: Jan. 5, 2017

(65) Prior Publication Data
US 2020/0056250 A1    Feb. 20, 2020

(30) Foreign Application Priority Data

Jun. 30, 2015 (GB) .................................. 1511470

(51) Int. Cl.
| | | |
|---|---|---|
| C12Q 1/68 | (2018.01) | |
| C12Q 1/70 | (2006.01) | |
| C12P 19/34 | (2006.01) | |
| B01L 3/00 | (2006.01) | |
| B01L 7/00 | (2006.01) | |
| C12Q 1/686 | (2018.01) | |

(52) U.S. Cl.
CPC ............ *C12Q 1/708* (2013.01); *C12Q 1/686* (2013.01); *C12Q 2600/112* (2013.01); *C12Q 2600/16* (2013.01)

(58) Field of Classification Search
CPC .................. C12Q 1/6851; C12Q 1/686; C12Q 2537/143; C12Q 2565/101; C12Q 1/6886
See application file for complete search history.

(56) References Cited

U.S. PATENT DOCUMENTS

| | | |
|---|---|---|
| 4,415,732 A | 11/1983 | Caruthers et al. |
| 4,458,066 A | 7/1984 | Caruthers et al. |
| 4,683,195 A | 7/1987 | Mullis et al. |
| 4,683,202 A | 7/1987 | Mullis |
| 4,849,332 A | 7/1989 | Lorincz |
| 4,973,679 A | 11/1990 | Caruthers et al. |
| 4,980,460 A | 12/1990 | Molko et al. |
| 5,364,758 A | 11/1994 | Meijer et al. |
| 5,447,839 A | 9/1995 | Manos et al. |
| 5,705,627 A | 1/1998 | Manos et al. |

FOREIGN PATENT DOCUMENTS

| | | |
|---|---|---|
| EP | 2508625 A1 | 10/2012 |
| WO | 2007057669 A2 | 5/2007 |
| WO | 2012116220 A2 | 8/2012 |

OTHER PUBLICATIONS

Tacaks et al., "Molecular beacon-based real-time PCR method for detection of 15 high-risk and 5 low-risk HPV types", Journal of Virological Methods, 2008, 149(1):153-162.*
Takacs, et al., "Molecular Beacon-Based Real-Time PCR Method for Detection of 15 High-Risk and 5 Low-Risk HPV Types," Journal of Virological Methods, 149(1): pp. 153-162 (Feb. 2008).
Lamarcq, L., et al., "Measurements of Human Papillomavirus Transcripts by Real Time Quantitative Reverse Transcription-Polymerase Chain Reaction in Samples Collected for Cervical Cancer Screening," The Journal of Molecular Diagonistics: JMD, 4(2): pp. 97-102 (May 2002).
Carcopino, X., et al., "Determination of HPV Type 16 and 18 Viral Load in Cervical Smears of Women Referred to Colposcopy," Journal of Medical Virology, 78(8): pp. 1131-1140 (Aug. 2006).
Yu, S., et al., "Comparison of Clinical Performances Among Roche Cobas HPV, RFMP HPV PapilloTyper and Hybrid Capture 2 Assays for Detection of High-Risk Types of Human Papillomavirus," Journal of Medical Virology, 87(9): pp. 1587-1593 (Apr. 2015).
Park, Y., et al., "Comparison of the Abbott RealTime High-Risk Human Papillomavirus (HPV), Roche Cobas HPV, and Hybrid Capture 2 Assays to Direct Sequencing and Genotyping of HPV DNA," Journal of Clinical Microbiology, 50(7): pp. 2359-2365 (Apr. 2012).
Devilliers, J. Virology 63:4898-4903, 1989.
Kleter B. et al., Am. J. of Pathology, vol. 153, No. 6, 1731-39 (1998).
Ozaki, et al, Nuc. Acids Res. 20: 5205-5214 (1992).
Agrawal, et al, Nuc. Acids Res, 18: 5419-5423 (1990).
Beaucage, et al., Tetrahedron 48: 2223-2311 (1992).
Innis, et al, editors, PCR Protocols, (Academic Press, New York, 1989.
Sambrook, et al, Molecular Cloning, Second Edition, (Cold Spring Harbour Laboratory, New York 1989).
Gut,et al, Virol. Methods 77(1): 37-46 (1999)).
Yajima, et al, Clin. Chem, 44(12): 2441-2445 (1998).
Martell, et al, J. Clin. Microbiol., 37(2): 327-332 (1999).
Preudhomme, et al, Leukemia, 13(6): 957-964 (1999)).

* cited by examiner

*Primary Examiner* — Barry A Chestnut
(74) *Attorney, Agent, or Firm* — Elmore Patent Law Group, P.C.; Carolyn S. Elmore; Mahreen Chaudhry Hoda

(57) ABSTRACT

This invention relates to the detection of human papillomavirus (HPV) genotypes, particularly genital human papillomavirus genotypes, using PCR related methods.

24 Claims, No Drawings
Specification includes a Sequence Listing.

SEQUENCE LISTING

<160> NUMBER OF SEQ ID NOS: 57

<210> SEQ ID NO 1
<211> LENGTH: 21
<212> TYPE: DNA
<213> ORGANISM: Artificial Sequence
<220> FEATURE:
<223> OTHER INFORMATION: Primer

<400> SEQUENCE: 1
tcatgcagga acatccagac t                                          21

<210> SEQ ID NO 2
<211> LENGTH: 20
<212> TYPE: DNA
<213> ORGANISM: Artificial Sequence
<220> FEATURE:
<223> OTHER INFORMATION: Primer

<400> SEQUENCE: 2
ccaaacttat tggggtcagg                                            20

<210> SEQ ID NO 3
<211> LENGTH: 25
<212> TYPE: DNA
<213> ORGANISM: Artificial Sequence
<220> FEATURE:
<223> OTHER INFORMATION: Probe

<400> SEQUENCE: 3
ttgcagttgg acatccctat tttcc                                      25

<210> SEQ ID NO 4
<211> LENGTH: 21

-continued

<212> TYPE: DNA
<213> ORGANISM: Artificial Sequence
<220> FEATURE:
<223> OTHER INFORMATION: Primer

<400> SEQUENCE: 4
tcatgctggc agctctagat t                                               21

<210> SEQ ID NO 5
<211> LENGTH: 22
<212> TYPE: DNA
<213> ORGANISM: Artificial Sequence
<220> FEATURE:
<223> OTHER INFORMATION: Primer

<400> SEQUENCE: 5
ggtcaggtaa ctgcaccctt aa                                              22

<210> SEQ ID NO 6
<211> LENGTH: 21
<212> TYPE: DNA
<213> ORGANISM: Artificial Sequence
<220> FEATURE:
<223> OTHER INFORMATION: Probe

<400> SEQUENCE: 6
agggttcctg caggtggtgg c                                               21

<210> SEQ ID NO 7
<211> LENGTH: 19
<212> TYPE: DNA
<213> ORGANISM: Artificial Sequence
<220> FEATURE:
<223> OTHER INFORMATION: Primer

<400> SEQUENCE: 7
gtggggacgc catctattc                                                  19

<210> SEQ ID NO 8
<211> LENGTH: 20
<212> TYPE: DNA
<213> ORGANISM: Artificial Sequence
<220> FEATURE:
<223> OTHER INFORMATION: Primer

<400> SEQUENCE: 8
tatgcgcgag gcatattcta                                                 20

<210> SEQ ID NO 9
<211> LENGTH: 20
<212> TYPE: DNA
<213> ORGANISM: Artificial Sequence
<220> FEATURE:
<223> OTHER INFORMATION: Probe

<400> SEQUENCE: 9
cagataccgg tgcgctgcgt                                                 20

<210> SEQ ID NO 10
<211> LENGTH: 18
<212> TYPE: DNA
<213> ORGANISM: Artificial Sequence
<220> FEATURE:
<223> OTHER INFORMATION: Primer

<400> SEQUENCE: 10
cacgcaggca gtgctagg                                                  18

<210> SEQ ID NO 11
<211> LENGTH: 21
<212> TYPE: DNA
<213> ORGANISM: Artificial Sequence
<220> FEATURE:
<223> OTHER INFORMATION: Primer

<400> SEQUENCE: 11
tccaaatttg tttggatctg g                                              21

<210> SEQ ID NO 12
<211> LENGTH: 28
<212> TYPE: DNA
<213> ORGANISM: Artificial Sequence
<220> FEATURE:
<223> OTHER INFORMATION: Probe

<400> SEQUENCE: 12
cagtaggcca tccatattat tccatacc                                       28

<210> SEQ ID NO 13
<211> LENGTH: 23
<212> TYPE: DNA
<213> ORGANISM: Artificial Sequence
<220> FEATURE:
<223> OTHER INFORMATION: Primer

<400> SEQUENCE: 13
gctggtagtt ccagacttct tgc                                            23

<210> SEQ ID NO 14
<211> LENGTH: 26
<212> TYPE: DNA
<213> ORGANISM: Artificial Sequence
<220> FEATURE:
<223> OTHER INFORMATION: Primer

<400> SEQUENCE: 14
ccaaatttat taggatctgg taaacg                                         26

<210> SEQ ID NO 15
<211> LENGTH: 25
<212> TYPE: DNA
<213> ORGANISM: Artificial Sequence
<220> FEATURE:
<223> OTHER INFORMATION: PRobe

<400> SEQUENCE: 15
tggtacccaa agtatcaggc ttgca                                          25

<210> SEQ ID NO 16
<211> LENGTH: 21
<212> TYPE: DNA
<213> ORGANISM: Artificial Sequence
<220> FEATURE:
<223> OTHER INFORMATION: Primer

<400> SEQUENCE: 16
ttatgcaggc agttctcgat t                                              21

<210> SEQ ID NO 17
<211> LENGTH: 20
<212> TYPE: DNA
<213> ORGANISM: Artificial Sequence

```
<220> FEATURE:
<223> OTHER INFORMATION: Primer

<400> SEQUENCE: 17
gggtccggca atttaattct                                              20

<210> SEQ ID NO 18
<211> LENGTH: 34
<212> TYPE: DNA
<213> ORGANISM: Artificial Sequence
<220> FEATURE:
<223> OTHER INFORMATION: Probe

<400> SEQUENCE: 18
aggacatccc tattttctta ttaaaaacac cagt                              34

<210> SEQ ID NO 19
<211> LENGTH: 20
<212> TYPE: DNA
<213> ORGANISM: Artificial Sequence
<220> FEATURE:
<223> OTHER INFORMATION: Primer

<400> SEQUENCE: 19
tatcatgcag gcagttcacg                                              20

<210> SEQ ID NO 20
<211> LENGTH: 22
<212> TYPE: DNA
<213> ORGANISM: Artificial Sequence
<220> FEATURE:
<223> OTHER INFORMATION: Primer

<400> SEQUENCE: 20
aaacttatta gggtcgggca ac                                           22

<210> SEQ ID NO 21
<211> LENGTH: 26
<212> TYPE: DNA
<213> ORGANISM: Artificial Sequence
<220> FEATURE:
<223> OTHER INFORMATION: Probe

<400> SEQUENCE: 21
ggacaatacc aaaacaaaca ttccca                                       26

<210> SEQ ID NO 22
<211> LENGTH: 20
<212> TYPE: DNA
<213> ORGANISM: Artificial Sequence
<220> FEATURE:
<223> OTHER INFORMATION: Primer

<400> SEQUENCE: 22
tgctggcagt tccagacttt                                              20

<210> SEQ ID NO 23
<211> LENGTH: 23
<212> TYPE: DNA
<213> ORGANISM: Artificial Sequence
<220> FEATURE:
<223> OTHER INFORMATION: Primer

<400> SEQUENCE: 23
aaaccaaatt tattgggatc agg                                          23
```

```
<210> SEQ ID NO 24
<211> LENGTH: 29
<212> TYPE: DNA
<213> ORGANISM: Artificial Sequence
<220> FEATURE:
<223> OTHER INFORMATION: Probe

<400> SEQUENCE: 24
tcccaaggta tcaggcttac agtataggg                              29

<210> SEQ ID NO 25
<211> LENGTH: 19
<212> TYPE: DNA
<213> ORGANISM: Artificial Sequence
<220> FEATURE:
<223> OTHER INFORMATION: Primer

<400> SEQUENCE: 25
acgcaggcag ttccagact                                         19

<210> SEQ ID NO 26
<211> LENGTH: 20
<212> TYPE: DNA
<213> ORGANISM: Artificial Sequence
<220> FEATURE:
<223> OTHER INFORMATION: Primer

<400> SEQUENCE: 26
ggccaaattt attgggatca                                        20

<210> SEQ ID NO 27
<211> LENGTH: 27
<212> TYPE: DNA
<213> ORGANISM: Artificial Sequence
<220> FEATURE:
<223> OTHER INFORMATION: Probe

<400> SEQUENCE: 27
tggtagacag gatgttccta aggtgtc                                27

<210> SEQ ID NO 28
<211> LENGTH: 19
<212> TYPE: DNA
<213> ORGANISM: Artificial Sequence
<220> FEATURE:
<223> OTHER INFORMATION: Primer

<400> SEQUENCE: 28
gtggggacgc catctattc                                         19

<210> SEQ ID NO 29
<211> LENGTH: 20
<212> TYPE: DNA
<213> ORGANISM: Artificial Sequence
<220> FEATURE:
<223> OTHER INFORMATION: Primer

<400> SEQUENCE: 29
tatgcgcgag gcatattcta                                        20

<210> SEQ ID NO 30
<211> LENGTH: 20
<212> TYPE: DNA
<213> ORGANISM: Artificial Sequence
<220> FEATURE:
<223> OTHER INFORMATION: Probe
```

```
<400> SEQUENCE: 30
cagataccgg tgcgctgcgt                                              20

<210> SEQ ID NO 31
<211> LENGTH: 20
<212> TYPE: DNA
<213> ORGANISM: Artificial Sequence
<220> FEATURE:
<223> OTHER INFORMATION: Primer

<400> SEQUENCE: 31
tcatgcaggc agttctaggc                                              20

<210> SEQ ID NO 32
<211> LENGTH: 26
<212> TYPE: DNA
<213> ORGANISM: Artificial Sequence
<220> FEATURE:
<223> OTHER INFORMATION: Primer

<400> SEQUENCE: 32
gaaatccaaa cttattagga tctggt                                       26

<210> SEQ ID NO 33
<211> LENGTH: 27
<212> TYPE: DNA
<213> ORGANISM: Artificial Sequence
<220> FEATURE:
<223> OTHER INFORMATION: Probe

<400> SEQUENCE: 33
agcagtaccc aaggtatctg gtttgca                                      27

<210> SEQ ID NO 34
<211> LENGTH: 22
<212> TYPE: DNA
<213> ORGANISM: Artificial Sequence
<220> FEATURE:
<223> OTHER INFORMATION: Primer

<400> SEQUENCE: 34
atgctggcag ctctagatta tt                                           22

<210> SEQ ID NO 35
<211> LENGTH: 20
<212> TYPE: DNA
<213> ORGANISM: Artificial Sequence
<220> FEATURE:
<223> OTHER INFORMATION: Primer

<400> SEQUENCE: 35
ttaggatcgg gcaatgtcac                                              20

<210> SEQ ID NO 36
<211> LENGTH: 21
<212> TYPE: DNA
<213> ORGANISM: Artificial Sequence
<220> FEATURE:
<223> OTHER INFORMATION: Probe

<400> SEQUENCE: 36
tgaatggtgg tcgcaagcag g                                            21

<210> SEQ ID NO 37
```

-continued

<210> SEQ ID NO 37
<211> LENGTH: 20
<212> TYPE: DNA
<213> ORGANISM: Artificial Sequence
<220> FEATURE:
<223> OTHER INFORMATION: Primer

<400> SEQUENCE: 37
gcaggcagtt cccgattatt                                              20

<210> SEQ ID NO 38
<211> LENGTH: 25
<212> TYPE: DNA
<213> ORGANISM: Artificial Sequence
<220> FEATURE:
<223> OTHER INFORMATION: Primer

<400> SEQUENCE: 38
tccaaattta ttaggatcgg gtaaa                                         25

<210> SEQ ID NO 39
<211> LENGTH: 24
<212> TYPE: DNA
<213> ORGANISM: Artificial Sequence
<220> FEATURE:
<223> OTHER INFORMATION: Probe

<400> SEQUENCE: 39
caggctgttc ctaaggtatc cgca                                          24

<210> SEQ ID NO 40
<211> LENGTH: 20
<212> TYPE: DNA
<213> ORGANISM: Artificial Sequence
<220> FEATURE:
<223> OTHER INFORMATION: Primer

<400> SEQUENCE: 40
tgcaggcagt tccagactaa                                               20

<210> SEQ ID NO 41
<211> LENGTH: 25
<212> TYPE: DNA
<213> ORGANISM: Artificial Sequence
<220> FEATURE:
<223> OTHER INFORMATION: Primer

<400> SEQUENCE: 41
gagtccaaac ttgttaggat ctggt                                         25

<210> SEQ ID NO 42
<211> LENGTH: 22
<212> TYPE: DNA
<213> ORGANISM: Artificial Sequence
<220> FEATURE:
<223> OTHER INFORMATION: PRobe

<400> SEQUENCE: 42
cctcaacgcg tgctgctatt cc                                            22

<210> SEQ ID NO 43
<211> LENGTH: 21
<212> TYPE: DNA
<213> ORGANISM: Artificial Sequence
<220> FEATURE:
<223> OTHER INFORMATION: Primer

<400> SEQUENCE: 43
tgcaggtagc tctaggttgc t                                              21

<210> SEQ ID NO 44
<211> LENGTH: 20
<212> TYPE: DNA
<213> ORGANISM: Artificial Sequence
<220> FEATURE:
<223> OTHER INFORMATION: Primer

<400> SEQUENCE: 44
taggatcagg caaccgtacc                                                20

<210> SEQ ID NO 45
<211> LENGTH: 27
<212> TYPE: DNA
<213> ORGANISM: Artificial Sequence
<220> FEATURE:
<223> OTHER INFORMATION: Probe

<400> SEQUENCE: 45
caaatctggt accaaaacaa acatccc                                        27

<210> SEQ ID NO 46
<211> LENGTH: 26
<212> TYPE: DNA
<213> ORGANISM: Artificial Sequence
<220> FEATURE:
<223> OTHER INFORMATION: Primer

<400> SEQUENCE: 46
tgctggtaca tctaggttat taactg                                         26

<210> SEQ ID NO 47
<211> LENGTH: 28
<212> TYPE: DNA
<213> ORGANISM: Artificial Sequence
<220> FEATURE:
<223> OTHER INFORMATION: Primer

<400> SEQUENCE: 47
caggaacact aaatttatta ggatcagg                                       28

<210> SEQ ID NO 48
<211> LENGTH: 20
<212> TYPE: DNA
<213> ORGANISM: Artificial Sequence
<220> FEATURE:
<223> OTHER INFORMATION: Probe

<400> SEQUENCE: 48
ctatgtctgg gggccgcaag                                                20

<210> SEQ ID NO 49
<211> LENGTH: 19
<212> TYPE: DNA
<213> ORGANISM: Artificial Sequence
<220> FEATURE:
<223> OTHER INFORMATION: Primer

<400> SEQUENCE: 49
gtggggacgc catctattc                                                 19

<210> SEQ ID NO 50
<211> LENGTH: 20
<212> TYPE: DNA

```
<213> ORGANISM: Artificial Sequence
<220> FEATURE:
<223> OTHER INFORMATION: Primer

<400> SEQUENCE: 50
tatgcgcgag gcatattcta                                              20

<210> SEQ ID NO 51
<211> LENGTH: 20
<212> TYPE: DNA
<213> ORGANISM: Artificial Sequence
<220> FEATURE:
<223> OTHER INFORMATION: Probe

<400> SEQUENCE: 51
cagataccgg tgcgctgcgt                                              20

<210> SEQ ID NO 52
<211> LENGTH: 24
<212> TYPE: DNA
<213> ORGANISM: Artificial Sequence
<220> FEATURE:
<223> OTHER INFORMATION: Primer

<400> SEQUENCE: 52
tctgaaaggt tacttcaagg acaa                                         24

<210> SEQ ID NO 53
<211> LENGTH: 20
<212> TYPE: DNA
<213> ORGANISM: Artificial Sequence
<220> FEATURE:
<223> OTHER INFORMATION: Primer

<400> SEQUENCE: 53
catcgcctct gggctaatag                                              20

<210> SEQ ID NO 54
<211> LENGTH: 26
<212> TYPE: DNA
<213> ORGANISM: Artificial Sequence
<220> FEATURE:
<223> OTHER INFORMATION: Probe

<400> SEQUENCE: 54
ctgtaagagc agatccctgg acaggc                                       26

<210> SEQ ID NO 55
<211> LENGTH: 19
<212> TYPE: DNA
<213> ORGANISM: Artificial Sequence
<220> FEATURE:
<223> OTHER INFORMATION: Primer

<400> SEQUENCE: 55
gtggggacgc catctattc                                               19

<210> SEQ ID NO 56
<211> LENGTH: 20
<212> TYPE: DNA
<213> ORGANISM: Artificial Sequence
<220> FEATURE:
<223> OTHER INFORMATION: Primer

<400> SEQUENCE: 56
tatgcgcgag gcatattcta                                              20
```

```
<210> SEQ ID NO 57
<211> LENGTH: 20
<212> TYPE: DNA
<213> ORGANISM: Artificial Sequence
<220> FEATURE:
<223> OTHER INFORMATION: Probe

<400> SEQUENCE: 57
cagataccgg tgcgctgcgt                                              20
```

HPV DETECTION METHOD

This invention relates to the detection of human papillomavirus (HPV) genotypes, particularly genital human papillomavirus genotypes.

Human Papillomavirus and its Significance

According to the World Health Organization (WHO), cervical cancer is the second most common cause of cancer death in women. The presence of HPV infection has been implicated in more than 99% of cervical cancers worldwide. As estimated, more than 500,000 women worldwide develop cervical cancer in every year, and more than 273,000 of the cases are fatal. Even with Pap screening programs, a significant number of women die from cervical cancer each year.

HPV infection is the most frequent sexually transmitted disease (STD) worldwide, and up to 60% of sexually active women will be infected by HPV in the genital tract once in their lifetime. Irrespective of HPV infection status, fewer than 1 in 10,000 women will develop invasive cervical cancer. The fact that most HPV-infected women do not develop cytological anomalies or cancer underlines the importance of factors modulating the progression of cervical disease to cancer in HPV-infected women. These factors may include the HPV genotype and molecular variant, the HPV viral load, persistence of HPV infection, co-infection with other STD agents, the immune status of the host and environmental factors such as smoking.

Papillomaviruses are small DNA viruses that infect mammalian epithelial cells, causing epithelial proliferative lesions which may be benign, e.g., fibropapillomas (warts), or which may be malignant. All papillomaviruses are similar in that the genome size, organization, open reading frames, and protein functions are shared. Many, but not all, genome regions are conserved among the various papillomaviruses.

Because of the close association between the papillomavirus life cycle and the differentiation state of the host cell, the details of the papillomavirus life cycle have not been completely elucidated. It is known that papillomaviruses infect host epithelial basal cells, where the viral genomes become established and are maintained as low copy-number episomes that replicate in coordination with host cell replication. As the infected cells differentiate into keratinocytes, viral DNA is amplified, the late genes are induced, and vegetative replication of the papillomavirus follows.

Papillomaviruses infect a wide variety of animals, including humans. The human papillomaviruses (HPV) (including Papillomaviridae family, Alpha-, Beta-, Gamma-, Delta-, Mupapillomavirus and unclassified Papillomaviridae genera) are common causes of sexually transmitted disease. Several types of HPV have been identified by DNA sequence data, and 96 HPV genotypes have been fully sequenced to date. Genotyping of HPV is based on DNA sequences of the L1, E6, and E7 genes. A 10% difference in sequence with respect to previously established strains is sufficient to define a new type of virus.

The heterogeneity of the human papillomavirus group is generally described in deVilliers, 1989, J. Virology 63:4898-4903, which is incorporated herein by reference. The genomes of numerous HPV types have been sequenced and/or characterized.

Based on the available molecular, clinical and epidemiologic data, a subset of HPVs are unequivocally the etiologic agents for cervical cancers and their precursors. HPVs have been detected in about 90% of cervical adenocarcinomas and squamous cell carcinomas. The majority of HPV infections clear spontaneously, but persistent infection with HPV DNA has been found in metastases arising from cervical tumours. Nevertheless known high-risk (or oncogenic) HPV types are a significant risk factor for cervical cancer and are increasingly recognized for their role in other cancers. Virtually all cervical cancers (99%) contain the genes of high-risk HPVs, most commonly types 16, 18, 31, and 45. Other high-risk types include types 31, 33, 35, 39, 45, 51, 52, 56, 58, 59, 68, and 73. HPVs 31, 33, 35, 51 and 52 are sometimes regarded as "intermediate risks" because they are more common in mild or severe dysplastic lesions than in carcinomas. Among the high-risk strains, HPV 16 and 18 are the most closely associated with cervical carcinoma. The HPV16 DNA has been found in more than 50% of squamous cell carcinomas, while the HPV18 DNA has been found in more than 50% of adenocarcinomas. However, the great majority of anogenital HPVs have oncogenic potential.

To date the clinical diseases, which are associated with HPV infections and the potential field of applications of HPV detection and typing methods include condyloma acuminatum, lichen sclerosis, squamous cell hyperplasia, vulvar intraepithelial neoplasia, squamous cell carcinoma, cervical intraepithelial neoplasia, cervical carcinoma, adenocarcinoma of the cervix, anal intraepithelial neoplasia, penile intraepithelial neoplasia, adenocarcinoma of the larynx, recurrent respiratory papillomatosis, and epidermodysplasias verruciformis. Recent evidence suggests that HPV may play a role in the development of prostate cancer in men as well.

Cervical cancer precursor lesions (intraepithelial lesions) or cytological abnormalities are tested using Papanicolaou Stain, known as the Pap smear after the inventor George Papanicolaou. The technique involves smearing cervical scrapes on a glass slide, and staining the cells obtained from the ano-genital tract with hematoxylin, a nuclear stain. The Pap smear, however, lacks repeatability and it is not sufficiently predictive of impending HPV-induced neoplasias. It has been shown that 25% of patients with advanced in situ carcinoma may present normal Pap smears a few years before diagnosis or the last negative cytology was uniformly positive in cervical cancer cases on re-examination. An increasingly prevalent problem is the occurrence of invasive cancer within 3 years of a negative Pap smear.

The current acceptable rate of false negatives (i.e., women who do have dysplasia according to an expert panel of pathologists looking at tissue biopsies rather than smear samples, but are not diagnosed that way during the routine smear screening) is roughly 5-10% but recent studies suggest that the actual rate may be much higher. Furthermore, in approximately 7-8% of cases, the Pap smear demonstrates atypical squamous cells of undetermined significance (AS-CUS). In an additional 20-30% of cases, the Pap smear may be insufficient for interpretation due to the presence of inflammatory cells. In the case of the cervix, flat warts (visualised by colposcopy) are suspected premalignant lesions. Histopathological progression of flat warts to carcinoma in situ and cervical cancer has been well described.

Intraepithelial lesions are common early events among women with incident HPV infection, and the interval between incident HPV-16 or HPV-18 infection and biopsy-confirmed CIN grade 2-3 appears to be relatively short. However studies have demonstrated that infection with high-risk HPV types is usually transient. Persistence of HPV infection substantially increases the risk of progression to high grade intraepithelial lesions and invasive disease.

The progression of the disease is variable and it is associated with the loss or persistence of HPV. Significant numbers of dysplastic lesions regress spontaneously, others fail to progress, while a few progress rapidly.

As a consequence of the preferential role of high-risk genotypes in cervical cancer and because of the different, consequential and characteristic type patterns for the other pathological conditions, both identification and typing of HPV is highly important. Additionally different types of high-risk HPV pose different risks to the affected individuals. For instance, HPV16 and HPV18 have been more consistently identified in higher grades of cervical dysplasia and carcinoma than other HPV types. HPV16 is also more prevalent in squamous carcinoma cases, and HPV18 is more prevalent in adenocarcinoma cases.

HPV Diagnostics

From 1980, several viral genomes have been cloned and used as type-specific probes in the diagnosis of HPVs. Filter hybridization techniques have been used to detect HPV DNA in cervical scrapes collected in parallel with samples for routine cytology. HPV DNA probes have been used in different hybridization-based assays such as Southern and hybrid Dot/Southern assays to detect HPV DNA in clinically-derived tissue samples. Additionally, purified biopsy DNA and in situ hybridizations in preserved tissue specimens, that is, direct localization within the intact cell of those sequences complementary to the nucleic acid probes have been demonstrated.

Numerous methods have been developed to detect human papillomavirus types using type-specific reactions, detecting one HPV type at a time. The Polymerase Chain reaction (PCR) has been used to amplify and detect the presence of HPV16 and HPV18 DNA, in particular to detect HPV16 in oral and cervical biopsies. A mixture of primers has been described for the specific amplification by PCR of HPV sequences in types 1a, 5, 6a, 8, 11, 16, 18, and 33. U.S. Pat. Nos. 4,683,195 and 4,683,202 disclose PCR and the use of PCR to detect the presence or absence of nucleic acid sequence in a sample.

U.S. Pat. No. 5,447,839, which is incorporated herein by reference, discloses a method for detection and typing of HPV. In this method, HPV DNA sequences in a sample are amplified by PCR using consensus primers which amplify both oncogenic and non-oncogenic HPV types. Thus, the presence of HPV in the sample is indicated by the formation of amplification products. HPV is then typed using type-specific DNA probes which hybridize with the amplified region of DNA. The type-specific hybridization probes disclosed in this patent are capable of identifying and distinguishing among five known oncogenic types of HPV, namely HPV-6, HPV-11, HPV-16, HPV-18 and HPV-33.

A variety of methods for detecting high-risk types of HPV have been devised. Many of these rely on the detection of unique sequences in the HPV genome. For example, DNA or RNA probes complementary to a portion of the genes of a particular high risk HPV strain have been reported in the art, as useful in screening for the presence of a particular strain of high-risk HPV in patient samples (U.S. Pat. No. 4,849,332, incorporated herein by reference). U.S. Pat. No. 5,705,627, incorporated herein by reference, reports use of PCR to amplify and detect HPV DNA using degenerate or mixed consensus primers, followed by typing using a mixture of genotype-specific DNA probes. Other examples of using consensus primers can be found in U.S. Pat. No. 5,364,758, and Kleter, B. et al., Am. J. of Pathology, vol. 153, No. 6, 1731-39 (1998). These references are also incorporated herein by reference.

There is a commercial method available, which is based on hybridisation and signal amplification. (Hybrid Capture II, Digene Corp.) However, this method reportedly has specificity problems due to the high sequence homology of some part of the HPV genomes.

The amplification based methods consist of a part responsible for sensitivity (amplification), which is separated from those parts responsible for specificity (detection by hybridisation). These techniques differ in the amplified genome section, the number of primers and the techniques of detection. The most often used amplification methods are GP5+-GP6+(general primer—GP), MY9-MY11, PGMY, SPF, L1C and the type specific PCR reactions. The most often used detection techniques are sequence specific hybridization, restriction fragment length polymorphism (RFLP) and line probe assay (LiPA). Sometimes, but rarely, sequencing or other methods are applied. The analytical properties of the amplifications vary within a wide range and are characterised by the number genotypes, which can be amplified, the analytical sensitivity, specificity of the amplification/detection of genotypes and also by the differences of sensitivities between genotypes.

HPV Real-Time PCR

Human papillomavirus-16 (HPV-16) viral load could be a biomarker predictive of the presence of high-grade cervical lesions. Several real-time PCR assays have been developed to accurately measure HPV-16 viral load (HPV-16 L1, HPV-16 E6, and HPV-16 E6 PG). The methods perform HPV detection in real-time, but detecting only one genotype at a time.

Identification of HPV DNA in patients with juvenile-onset recurrent respiratory papillomatosis was carried out using SYBR® Green real-time PCR. The method is used to detect multiple human papillomavirus genotypes in a real-time PCR reaction. However the amplification method is different from that described in the present invention. The amplicon produced is longer (approx. 450 bp), than is accepted for a probe based real-time amplification method in the art. The preferred length is 150 bp or less. The detection method is aspecific and unable to differentiate the genotypes reliably, which necessitates subsequent viral typing using real-time PCR with type-specific primers for HPV types 6, 11, 16, 18, 31, and 33. This again detects the types of human papillomavirus in isolates, but only one genotype at a time.

Consensus Primer Design Methods

Primers and probes that are used to detect only one human papillomavirus nucleic acid molecule, e.g., a nucleic acid molecule encoding a portion of the L1, can be designed using, for example, a computer program such as OLIGO (Molecular Biology Insights Inc., Cascade, Colo.) or Primer3. Appropriate features of these oligonucleotides are well known for those skilled in the art.

There is extensive literature on the general principles of PCR primer design, which have led to a number of software applications, most notably Primer3 and various extensions. A fast dynamic programming formulation for testing primers for pair-wise compatibility has also been developed. The application of multiplex PCR has increased steadily over the past decade, requiring more sophisticated primer selection protocols. Different algorithms may favor particular objectives, or may be designed for particular technology platforms. In general, the problem of identifying primer pairs to maximize the multiplexing level of a single assay has been shown to be NP-complete. An approximation algorithm that eliminates 3' base complementarity while addressing product size constraints has been presented.

There is a need for a real-time PCR method of HPV detection which is cheap, fast, robust, high throughput, which is specific enough to identify individual HPV types, whilst also being highly sensitive.

These objectives are contradictory goals because real-time PCR methods such as the Taqman system, need consensus primers which generally do not allow sensitivity for the different types of HPV to be adjusted. Therefore HPV type specific primers which act like consensus primers, i.e. cover very much the same region (of an ideal or theoretical HPV genome) had to be designed. If the primers were randomly placed or adjacently placed, the real-time PCR methods such as Taqman would not work.

This is not a simple design situation. A large amount of optimization was required to make sure type-specific primers cover each other as much as possible. This could not be achieved using convenient design software.

As well as considering the primer and probe sequences, all the usual design requirements of a high performing, robust real-time PCR methods such as a Taqman reaction have to be considered. This includes ensuring that the amplicon length is below 150 bp, having a melting temperature around 60° C. for primers, and 68° C. for the probes.

In addition the test needs to be highly sensitive without loosing analytical specificity.

HPV tests were previously required to be as specific as possible so that they did not to find too many HPV positive women who are not in need of treatment, (normally the ratio of infection versus lesion in need of treatment is 10 to 1.)

However, by using specific biomarkers, triage tests can now be used which can find the few pre-cancerous lesions in the many HPV positive women. HPV is now considered to be a risk factor. Therefore highly sensitive HPV tests are now required and more useful, because it is important to know which patients are at risk. Once a patient is identified as having HPV, they can be monitored or sent for further screening to identify the development of lesions at an early stage.

The present application provides a cheap, fast, robust, high throughput method which is capable of detecting and identifying all HPV whilst retaining a high degree of sensitivity. The method of the invention can be used as a screening test for high risk HPV infection. The use of genotype specific primers and probes provides a homogenous system for both screening and genotyping. Previous known methods are not capable of both screening and genotyping The present invention provides a method for detecting the presence of HPV, comprising amplifying a nucleic acid obtained from a sample utilizing one or more amplification mixtures, wherein the amplification mixtures are selected from:

(a) Amplification mixture 1 comprising
    (SEQ. ID NO: 1)
5'-TCATGCAGGAACATCCAGACT-3'

(SEQ. ID NO: 2)
5'-CCAAACTTATTGGGGTCAGG-3'

(SEQ. ID NO: 3)
5'-TTGCAGTTGGACATCCCTATTTTCC-3'

(b) Amplification mixture 2 comprising
    (SEQ. ID NO: 4)
5'-TCATGCTGGCAGCTCTAGATT-3'

(SEQ. ID NO: 5)
5'-GGTCAGGTAACTGCACCCTAAA-3'

(SEQ. ID NO: 6)
5'-AGGGTTCCTGCAGGTGGTGGC-3'

(c) Amplification mixture 3 comprising
    (SEQ. ID NO: 10)
5'-CACGCAGGCAGTGCTAGG-3'

(SEQ. ID NO: 11)
5'-TCCAAATTTGTTTGGATCTGG-3'

(SEQ. ID NO: 12)
5'-CAGTAGGCCATCCATATTATTCCATACC-3'

(d) Amplification mixture 4 comprising
    (SEQ. ID NO: 13)
5'-GCTGGTAGTTCCAGACTTCTTGC-3'

(SEQ. ID NO: 14)
5'-CCAAATTTATTAGGATCTGGTAAACG-3'

(SEQ. ID NO: 15)
5'-TGGTACCCAAAGTATCAGGCTTGCA-3'

(e) Amplification mixture 5 comprising
    (SEQ. ID NO: 16)
5'-TTATGCAGGCAGTTCTCGATT-3'

(SEQ. ID NO: 17)
5'-GGGTCCGGCAATTTAATTCT-3'

(SEQ. ID NO: 18)
5'-AGGACATCCCTATTTTTCTATTAAAAACACCAGT-3'

(f) Amplification mixture 6 comprising
    (SEQ. ID NO: 19)
5'-TATCATGCAGGCAGTTCACG-3'

(SEQ. ID NO: 20)
5'-AAACTTATTAGGGTCGGGCAAC-3'

(SEQ. ID NO: 21)
5'-GGACAATACCAAAACAAACATTCCCA-3'

(g) Amplification mixture 7 comprising
    (SEQ. ID NO: 22)
5'-TGCTGGCAGTTCCAGACTTT-3'

(SEQ. ID NO: 23)
5'-AAACCAAATTTATTGGGATCAGG-3'

(SEQ. ID NO: 24)
5'-TCCCAAGGTATCAGGCTTACAGTATAGGG-3'

(h) Amplification mixture 8 comprising
    (SEQ. ID NO: 25)
5'-ACGCAGGCAGTTCCAGACT-3'

(SEQ. ID NO: 26)
5'-GGCCAAATTTATTGGGATCA-3'

(SEQ. ID NO: 27)
5'-TGGTAGACAGGATGTTCCTAAGGTGTC-3';
or (i) Amplification mixture 9 comprising
    (SEQ. ID NO: 31)
5'-TCATGCAGGCAGTTCTAGGC-3'

(SEQ. ID NO: 32)
5'-GAAATCCAAACTTATTAGGATCTGGT-3'

(SEQ. ID NO: 33)
5'-AGCAGTACCCAAGGTATCTGGTTTGCA-3'

(j) Amplification mixture 10 comprising
    (SEQ. ID NO: 34)
5'-ATGCTGGCAGCTCTAGATTATT-3'

(SEQ. ID NO: 35)
5'-TTAGGATCGGGCAATGTCAC-3'

-continued (SEQ. ID NO: 36)
5'-TGAATGGTGGTCGCAAGCAGG-3'

(k) Amplification mixture 11 comprising
(SEQ. ID NO: 37)
5'-GCAGGCAGTTCCCGATTATT-3'

(SEQ. ID NO: 38)
5'-TCCAAATTTATTAGGATCGGGTAAA-3'

(SEQ. ID NO: 39)
5'-CAG GCT GTT CCT AAG GTA TCC GCA-3'

(l) Amplification mixture 12 comprising
(SEQ. ID NO: 40)
5'-TGCAGGCAGTTCCAGACTAA-3'

(SEQ. ID NO: 41)
5'-GAGTCCAAACTTGTTAGGATCTGGT-3'

(SEQ. ID NO: 42)
5'-CCTCAACGCGTGCTGCTATTCC-3'

(m) Amplification mixture 13 comprising
(SEQ. ID NO: 43)
5'-TGCAGGTAGCTCTAGGTTGCT-3'

(SEQ. ID NO: 44)
5'-TAGGATCAGGCAACCGTACC-3'

(SEQ. ID NO: 45)
CAAATCTGGTACCAAAACAAACATCCC-3'

(n) Amplification mixture 14 comprising
(SEQ. ID NO: 46)
TGCTGGTACATCTAGGTTATTAACTG-3'

(SEQ. ID NO: 47)
5'-CAGGAACACTAAATTTATTAGGATCAGG-3'

(SEQ. ID NO: 48)
5'-CTATGTCTGGGGGCCGCAAG.-3';

wherein SEQ ID No's: 3, 6, 12, 15, 18, 21, 24, 27, 33, 36, 39, 42, 45 and 48 are labelled with a quencher and dye, one at the 5' end and one at the 3' end. Preferably SEQ ID No's: 3, 6, 12, 15, 18, 21, 24, 27, 33, 36, 39, 42, 45 and 48 are labelled with a dye at the 5' end and a quencher at the 3' end.

The method may further comprise measuring the signal generated by the dye. The presence of a signal indicates that the HPV genotype being tested is present. If no signal is detected, the HPV genotype being tested is absent, and the sample comes from a subject who is not infected with HPV of the genotype being detected. The signal can be detected by exposing the sample to light of a suitable wavelength to induce fluorescent emission from the dye.

The present invention also provides a method for detecting the presence of HPV, comprising amplifying a nucleic acid obtained from a sample utilizing one or more amplification mixtures, wherein the amplification mixtures are selected from:

(a) Amplification mixture 15 comprising
(SEQ. ID NO: 1)
5'-TCATGCAGGAACATCCAGACT-3'

(SEQ. ID NO: 2)
5'-CCAAACTTATTGGGGTCAGG-3'

(SEQ. ID NO: 3)
5'-TTGCAGTTGGACATCCCTATTTTCC-3'

(SEQ. ID NO: 4)
5'-TCATGCTGGCAGCTCTAGATT-3'

(SEQ. ID NO: 5)
5'-GGTCAGGTAACTGCACCCTAAA-3'

(SEQ. ID NO: 6)
5'-AGGGTTCCTGCAGGTGGTGGC-3'

(b) Amplification mixture 16 comprising
(SEQ. ID NO: 10)
5'-CACGCAGGCAGTGCTAGG-3'

(SEQ. ID NO: 11)
5'-TCCAAATTTGTTTGGATCTGG-3'

(SEQ. ID NO: 12)
5'-CAGTAGGCCATCCATATTATTCCATACC-3'

(SEQ. ID NO: 13)
5'-GCTGGTAGTTCCAGACTTCTTGC-3'

(SEQ. ID NO: 14)
5'-CCAAATTTATTAGGATCTGGTAAACG-3'

(SEQ. ID NO: 15)
5'-TGGTACCCAAAGTATCAGGCTTGCA-3'

(SEQ. ID NO: 16)
5'-TTATGCAGGCAGTTCTCGATT-3'

(SEQ. ID NO: 17)
5'-GGGTCCGGCAATTTAATTCT-3'

(SEQ. ID NO: 18)
5'-AGGACATCCCTATTTTTCTATTAAAAACACCAGT-3'

(SEQ. ID NO: 19)
5'-TATCATGCAGGCAGTTCACG-3'

(SEQ. ID NO: 20)
5'-AAACTTATTAGGGTCGGGCAAC-3'

(SEQ. ID NO: 21)
5'-GGACAATACCAAAACAAACATTCCCA-3'

(SEQ. ID NO: 22)
5'-TGCTGGCAGTTCCAGACTTT-3'

(SEQ. ID NO: 23)
5'-AAACCAAATTTATTGGGATCAGG-3'

(SEQ. ID NO: 24)
5'-TCCCAAGGTATCAGGCTTACAGTATAGGG-3'

(SEQ. ID NO: 25)
5'-ACGCAGGCAGTTCCAGACT-3'

(SEQ. ID NO: 26)
5'-GGCCAAATTTATTGGGATCA-3'

(SEQ. ID NO: 27)
5'-TGGTAGACAGGATGTTCCTAAGGTGTC-3';
or (c) Amplification mixture 17 comprising
(SEQ. ID NO: 31)
5'-TCATGCAGGCAGTTCTAGGC-3'

(SEQ. ID NO: 32)
5'-GAAATCCAAACTTATTAGGATCTGGT-3'

(SEQ. ID NO: 33)
5'-AGCAGTACCCAAGGTATCTGGTTTGCA-3'

(SEQ. ID NO: 34)
5'-ATGCTGGCAGCTCTAGATTATT-3'

(SEQ. ID NO: 35)
5'-TTAGGATCGGGCAATGTCAC-3'

(SEQ. ID NO: 36)
5'-TGAATGGTGGTCGCAAGCAGG-3'

-continued

5'-GCAGGCAGTTCCCGATTATT-3' (SEQ. ID NO: 37)

5'-TCCAAATTTATTAGGATCGGGTAAA-3' (SEQ. ID NO: 38)

5'-CAG GCT GTT CCT AAG GTA TCC GCA-3' (SEQ. ID NO: 39)

5'-TGCAGGCAGTTCCAGACTAA-3' (SEQ. ID NO: 40)

5'-GAGTCCAAACTTGTTAGGATCTGGT-3' (SEQ. ID NO: 41)

5'-CCTCAACGCGTGCTGCTATTCC-3' (SEQ. ID NO: 42)

5'-TGCAGGTAGCTCTAGGTTGCT-3' (SEQ. ID NO: 43)

5'-TAGGATCAGGCAACCGTACC-3' (SEQ. ID NO: 44)

CAAATCTGGTACCAAAACAAACATCCC-3' (SEQ. ID NO: 45)

TGCTGGTACATCTAGGTTATTAACTG-3' (SEQ. ID NO: 46)

5'-CAGGAACACTAAATTTATTAGGATCAGG-3' (SEQ. ID NO: 47)

5'-CTATGTCTGGGGCCGCAAG.-3'; (SEQ. ID NO: 48)

wherein SEQ ID No's: 3, 6, 12, 15, 18, 21, 24, 27, 33, 36, 39, 42, 45 and 48 are labelled with a quencher and dye, one at the 5' end and one at the 3' end. Preferably SEQ ID No's: 3, 6, 12, 15, 18, 21, 24, 27, 33, 36, 39, 42, 45 and 48 are labelled with a dye at the 5' end and a quencher at the 3' end.

Preferably, the method further comprises amplifying the nucleic acid obtained from a sample with an amplification mixture capable of amplifying a human control gene, preferably the factor V leiden gene.

More preferably the amplification mixture capable of amplifying a human control gene comprises:

Amplification mixture 18 comprising

5'-TCTGAAAGGTTACTTCAAGGACAA-3' (SEQ. ID NO: 52)

5'-CATCGCCTCTGGGCTAATAG-3' (SEQ. ID NO: 53)

5'-CTGTAAGAGCAGATCCCTGGACAGGC-3' (SEQ. ID NO: 54)

Wherein SEQ ID No: 54 is labelled with a quencher and dye, one at the 5' end and one at the 3' end. Preferably, SEQ ID No: 54 is labelled with a dye at the 5' end and a quencher at the 3' end.

The method comprises one or more reactions. The method may comprise 1, 2, 3, 4 or more reactions, using any combination of amplification mixtures 1 to 18. Preferably, the method may comprise 1, 2, 3, or 4 reactions, using any combination of amplification mixtures 15-18. Preferably each reaction is carried out separately using an amplification mixture, i.e. each amplification mixture is reacted with a nucleic acid sample. Preferably two or more amplification mixtures are not mixed together in one reaction, and the reaction for each amplification mixture is carried out in a separate vessel. Alternatively, several amplification mixtures selected from amplification mixtures 1-17, for example up to 3 amplification mixtures, optionally together with an amplification mixture capable of amplifying a human control gene, such as amplification mixture 18, and/or an internal control gene amplification mixture can be used in one reaction. One, two, three or more mixtures, optionally with the human control gene mixture and/or an internal control gene mixture can be placed in one vessel. Preferably up to 3 amplification mixtures selected from amplification mixtures 1-17 are used in one reaction. As used herein "vessel" refers to a reaction chamber. This can be a well within a multiple well plate, or a single isolated container such as an eppendorf tube.

Each amplification mixture comprises primers and probes for amplifying and identifying any HPV nucleic acid sequences present. Amplification mixture no. 15 targets HPV 16 and 18, Amplification mixture no. 16 targets HPV 31, 33, 52, 56, 58, 59; Amplification mixture no. 17 targets HPV 35, 39, 45, 51, 66, 68; and Amplification mixture reaction no. 18 targets a human control gene such as the factor V leiden gene. Each reaction preferably has internal controls as well.

Preferably, the amplification mixtures further comprises one or more internal control primers. For example amplification mixtures 1-18 may further comprise Seq. ID Nos 7, 8 and 9, wherein SEQ ID No: 9 is labelled with a quencher and dye, one at the 5' end and one at the 3' end. Preferably, SEQ ID No: 9 is labelled with a dye at the 5' end and a quencher at the 3' end. For example amplification mixture 15 preferably further comprises:

5'-GTGGGGACGCCATCTATTC-3' (SEQ. ID NO: 7)

5'-TATGCGCGAGGCATATTCTA-3' (SEQ. ID NO: 8)

5'-CAGATACCGGTGCGCTGCGT-3';; (SEQ. ID NO: 9)
and/or

Amplification mixture 16 further comprises

5'-GTGGGGACGCCATCTATTC-3 (SEQ. ID NO: 28)

5'-TATGCGCGAGGCATATTCTA-3 (SEQ. ID NO: 29)

5'-CAGATACCGGTGCGCTGCGT-3';; (SEQ. ID NO: 30)
and/or

Amplification mixture 17 further comprises

5'-GTGGGGACGCCATCTATTC-3' (SEQ. ID NO: 49)

5'-TATGCGCGAGGCATATTCTA-3' (SEQ. ID NO: 50)

5'-CAGATACCGGTGCGCTGCGT-3'; (SEQ. ID NO: 51)
and/or

Amplification mixture 18 further comprises

5'-GTGGGGACGCCATCTATTC-3' (SEQ. ID NO: 55)

5'-TATGCGCGAGGCATATTCTA-3' (SEQ. ID NO: 56)

5'-CAGATACCGGTGCGCTGCGT-3' (SEQ. ID NO: 57)

Wherein SEQ ID No's: 9, 30, 51 and 57 are labelled with a quencher and dye, one at the 5' end and one at the 3' end.

Preferably SEQ ID No's: 9, 30, 51 and 57 are labelled with a dye at the 5' end and a quencher at the 3' end.

Preferably amplification mixture 15 consists of SEQ. ID No's: 1-6; and/or Amplification mixture 16 consists of SEQ. ID No's: 10-27; and/or Amplification mixture 17 consists of SEQ. ID No's: 31-48; and/or Amplification mixture 18 consists of SEQ. ID No's: 52-54.

More preferably amplification mixture 15 consists of SEQ. ID No's: 1-9; and/or Amplification mixture 16 consists of SEQ. ID No's: 10-30; and/or Amplification mixture 17 consists of SEQ. ID No's: 31-51; and/or Amplification mixture 18 consists of SEQ. ID No's: 52-57.

Oligonucleotide primers and probes can be synthesised by a number of approaches, e.g. Ozaki et al, *Nuc. Acids Res.* 20: 5205-5214 (1992); Agrawal et al, *Nuc. Acids Res.* 18: 5419-5423 (1990) or the like. Conveniently, the oligonucleotide primers and probes are synthesised on an automated DNA synthesiser, e.g. an Applied Biosystems, Inc., Foster City, Calif. model 392 or 394 DNA/RNA synthesiser using standard chemistries such as phosphoramidite chemistry (Beaucage and Iyer, *Tetrahedron* 48: 2223-2311 (1992), U.S. Pat. Nos. 4,980,460, 4,725,677, 4,415,732, 4,458,066 and 4,973,679).

SEQ. ID NOs: 3, 6, 9, 12, 15, 18, 21, 24, 27, 30, 33, 36, 39, 42, 45, 48, 51, 54 and 57 are probes. The probes used in the amplification mixtures are labelled with a quencher and dye, one at the 5' end and one at the 3' end. Therefore the probes may be labelled with a dye at the 5' end and a quencher at the 3' end or the probes may be labelled with a quencher at the 5' end and a dye at the 3' end Preferably the probes used in the amplification mixtures are labelled with a dye at the 5' end and a quencher at the 3' end. Preferably the dye is a fluorescent dye. The quencher and/or dye are removed from the probe during the amplification process by the polymerase, such as Taq polymerase, and therefore the signal from the dye can be detected. "At end 5' end" and "at the 3' end" mean that the dye or quencher are attached the the nucleotide at the 5' end or 3' end of the probe respectively.

As used herein, a "quencher" is a moiety which decreases the fluorescence emitted by the fluorescent label. This includes complete and partial inhibition of the emission of the fluorescence. The degree of inhibition is not important as long as a change in fluorescence can be detected once the quencher is removed.

The quenching moiety is preferably selected from the group consisting of tetramethylrhodamine (TAMRA) optionally substituted phenyls, naphthyls, anthracenyls, benzothiazoles, benzoxazoles, or benzimidazoles, pyrenes, anthracenes, naphthalenes, acridines, stilbenes, indoles, benzindoles, oxazoles, benzoxazoles, thiazoles, benzothiazoles, 4-amino-7-nitrobenz-2-oxa-1,3-diazoles, cyanines, carbocyanines, carbostyryls, porphyrins, salicylates, anthranilates, azulenes, perylenes, pyridines, quinolines, coumarins, polyazaindacenes, xanthenes, oxazines, benzoxazines, carbazines, phenalenones, benzphenalenones, carbazines, oxazines, 4-bora-3a,4a-diaza-s-indacenes, fluorophoresceins, rhodamines, rhodols, 5-carboxyfluorophoresceins, 5-(2'-aminoethyl) aminonapthalene-1-sulfonic acids (EDANS), anthranilamides, terbium chelates, Reactive Red 4, dabcyls, nitrotyrosines, malachite greens, Texas reds, dinitrobenzenes, ATTO dyes, EVO Dyes, DYO Dyes, Alexa dyes and BODIPY dyes. Preferably the quencher is selected from QSY® available from Life technologies Preferably the dye is a fluorescent dye. Representative donor fluorescent dyes include 6-carboxyfluorophoresceins (FAM) tetrachlorofluorescein, (TET), fluorescein, Lucifer Yellow, B-phycoerythrin, 9-acridineisothiocyanate, Lucifer Yellow VS, 4-acetamido-4'-isothio-cyanatostilbene-2,2'-disulfonic acid, 7-diethylamino-3-(4'-isothiocyanatophenyl)-4-methylcoumarin, succinimdyl 1-pyrenebutyrate, 4-acet-amido-4'-isothiocyanatostilbene-2,2'-disulfonic acid derivatives, optionally substituted pyrenes, anthracenes, naphthalenes, acridines, stilbenes, indoles, benzindoles, oxazoles, benzoxazoles, thiazoles, benzothiazoles, 4-amino-7-nitrobenz-2-oxa-1,3-diazoles, cyanines, carbocyanines, carbostyryls, porphyrins, salicylates, anthranilates, azulenes, perylenes, pyridines, quinolines, coumarins, polyazaindacenes, xanthenes, oxazines, benzoxazines, carbazines, phenalenones, benzphenalenones, carbazines, oxazines, 4-bora-3a,4a-diaza-s-indacenes, fluorophoresceins, rhodamines, rhodols, 5-carboxyfluorophoresceins (FAM), 5-(2'-aminoethyl) aminonapthalene-1-sulfonic acids (EDANS), anthranilamides, terbium chelates, Reactive Red 4, Texas reds, ATTO dyes, EVO Dyes, DYO Dyes, Alexa dyes and BODIPY dyes. Preferably the dyes are selected from FAM®, VIC®, ABY®, and JUN® available from Life technologies. Tetramethylrhodamine (TAMRA) can act as a dye as well as a quencher, depending on the combination of dye/quencher. Suitable dye/quencher combinations are known to the skilled person.

Different probes within one amplification mixture can be labelled with the same or different dyes. If different coloured dyes are used for the different probes in the mixture, the presence of different HPV genotypes can be detected. For example if the probes in Amplification mixture 15 are labelled with different coloured dyes, it is possible to identify whether HPV16, HPV 18 or both genotypes are present in a sample.

The method can be carried out using two or more amplification mixtures. Preferably a separate reaction is carried out for each amplification mixture. For example where the method uses two amplification mixtures, two reactions are carried out, each reaction in a separate chamber. Alternatively up to to 3 amplification mixtures selected from mixtures 1 to 17, optionally with an internal control amplification mixture (e.g. SEQ. ID Nos: 7, 8, and 9) and/or a mixture capable of amplifying a human control gene (e.g amplification mixture 18) can be mixed together in one reaction, in a single reaction chamber. The amplification reactions can be carried out concurrently i.e. at the same time, or sequentially i.e. one after another.

Preferably the nucleic acid is amplified utilizing PCR; more preferably real-time PCR. Preferably the amplification is carried out using the polymerase chain reaction (PCR). The amplification reaction may be PCR (see for example U.S. Pat. Nos. 4,683,195 and 4,683,202, and Innis et al, editors, PCR Protocols, (Academic Press, New York, 1989; Sambrook et al, Molecular Cloning, Second Edition, (Cold Spring Harbour Laboratory, New York 1989)). PCR can also be used when RNA has been isolated and converted, preferably by reverse transcription, to cDNA. Preferably, PCR is carried out using Taq DNA polymerase, e.g. Amplitaq™ (Perkin-Elmer, Norwalk, Conn.). Taq polymerase can also be obtained from MBI Fermentas, Perkin Elmer, Boehringer Mannheim and Beckman Instruments. An equivalent, preferably thermostable, DNA polymerase may also be used in the method of the present invention, such as Tfl (*Thermus flavus*) polymerase (Gut et al, *Virol. Methods* 77(1): 37-46 (1999)).

Alternatively, the amplification reaction may be RT-PCR (Yajima et al, *Clin. Chem*, 44(12): 2441-2445 (1998); Martell et al, *J. Clin. Microbiol.*, 37(2): 327-332 (1999); Gut et al, *Virol. Methods* 77(1): 37-46 (1999); Predhomme et al, Leukemia, 13(6): 957-964 (1999)), in which RNA is reverse transcribed into cDNA which is then subjected to PCR amplification.

As is well-known, PCR involves the extraction and denaturation (preferably by heat) of a sample of DNA (or RNA). A molar excess of oligonucleotide primers is added, along with a polymerase, which may be heat-stable, and dNTPs for forming the amplified sequence. The oligonucleotide primers are designed to hybridise to opposite ends of the sequence desired for amplification. In the first round of amplification, the polymerase replicates the DNA to produce two "long products," which begin with the respective primers. The total DNA, which includes the two long products and the two original strands, is then denatured and a second round of polymerisation is carried out (for example, by lowering the temperature). The result of the second round is the two original strands, the two long products from the first round, two new long products (produced from the original strands), and two "short products" produced from the long products. These short products have the sequence of the target sequence (sense or antisense) with a primer at each end. For each additional amplification round, the number of short products grows exponentially, each round producing two additional long products and a number of short products equal to the sum of the long and short products remaining at the end of the previous round.

Preferably the nucleic acid is amplified utilizing the Taqman system. TAQMAN™ technology detects the presence or absence of an amplification product, and hence, the presence or absence of human papillomavirus. TAQMAN™ technology utilizes one single-stranded hybridization probe labelled with two fluorescent moieties. When a first fluorescent moiety is excited with light of a suitable wavelength, the absorbed energy is transferred to a second fluorescent moiety according to the principles of FRET. The second fluorescent moiety is generally a quencher molecule. During the annealing step of the PCR reaction, the labelled hybridization probe binds to the target DNA and is degraded by the 5' to 3' exonuclease activity of the Taq Polymerase during the subsequent elongation phase. As a result, the excited fluorescent moiety and the second fluorescent moiety become spatially separated from one another. As a consequence, upon excitation of the first fluorescent moiety in the absence of the second fluorescent, the fluorescence emission from the first fluorescent moiety is detectably altered. For example, if the second fluorescent moiety is a quencher, the fluorescence emission from the first fluorescent moiety increases and thus can be detected. By way of example, an ABI PRISM™ 7700 Sequence Detection System (Applied Biosystems, Foster City, Calif.) uses TAQMAN™ technology, and is suitable for performing the methods for detecting human papillomavirus. Information on PCR amplification and detection using an ABI PRISM™ 7700 system can be found on Applied Biosystems' website.

The methods of the present invention are carried out on nucleic acids obtained from a biological sample. Representative biological samples include cervical scraping, biopsies, smear or paraffin tissue sections, other scrapings of anatomical sites where human papillomavirus infection takes place and urine. Preferably the sample is selected from bronchial aspirates, urine, prostata massate, ejaculatum, blood and cervical, vulvar, anal, genital, skin or laryngeal cytological samples, scrapings or biopsies. Preferably the sample is a cervical scraping, such as obtained during a Pap smear test. Nucleic acids can be isolated from the sample using conventional method.

As used herein, "nucleic acid" refers to DNA and RNA in its various forms such as mRNA, and hnRNA. The nucleic acid can be single stranded or double stranded.

Preferred amplification mixtures comprise or consist of the following

```
Amplification mixture A

HPV16/tqm4/F:
TCATGCAGGAACATCCAGACT

HPV16/tqm4/R:
CCAAACTTATTGGGGTCAGG

HPV16Tqm/T1/VIC/Q:
5'-VIC-TTGCAGTTGGACATCCCTATTTTCC-QSY-3'

HPV18/tqm4/F:
TCATGCTGGCAGCTCTAGATT

HPV18/tqm4/R:
GGTCAGGTAACTGCACCCTAAA

HPV18Tqm/T2/FAM/Q
5'-FAM-AGGGTTCCTGCAGGTGGTGGC-QSY-3

TQMIC/hdv/F1:
5-gtggggacgccatctattc-3

TQMIC/hdv/R1:
5-tatgcgcgaggcatattcta-3

TQMIC/T1/JUN/Q:
5-CY5-CAGATACCGGTGCGCTGCGT-QSY-3

Amplification mixture B

HPV31/tqm4/F2:
CACGCAGGCAGTGCTAGG

HPV31/tqm4/R:
TCCAAATTTGTTTGGATCTGG

HPV31Tqm/T2/VIC/Q:
5'-V1C-CAGTAGGCCATCCATATTATTCCATACC-QSY-3'

HPV33/tqm4/F:
GCTGGTAGTTCCAGACTTCTTGC

HPV33/tqm4/R:
CCAAATTTATTAGGATCTGGTAAACG

HPV33Tqm/T1/ABY/Q:
5'-ABY-TGGTACCCAAAGTATCAGGCTTGCA-QSY-3'

HPV52/tqm4/F:
TTATGCAGGCAGTTCTCGATT

HPV52/tqm4/R:
GGGTCCGGCAATTTAATTCT

HPV52Tqm/T1/ABY/Q:
5'-ABY-AGGACATCCCTATTTTCTATTAAAAACACCAGT-QSY-3'

HPV56/tqm4/F:
TATCATGCAGGCAGTTCACG

HPV56/tqm4/R:
AAACTTATTAGGGTCGGGCAAC

HPV56Tqm/T2/ABY/Q:
5'-ABY-GGACAATACCAAAACAAACATTCCCA-QSY-3'

HPV58/tqm4/F:
TGCTGGCAGTTCCAGACTTT

HPV58/tqm4/R:
AAACCAAATTTATTGGGATCAGG
```

HPV58Tqm/T1/FAM/Q:
5'-FAM-TCCCAAGGTATCAGGCTTACAGTATAGGG-QSY-3'

HPV59/tqm4/F:
ACGCAGGCAGTTCCAGACT

HPV59/tqm4/R:
GGCCAAATTTATTGGGATCA

HPV59Tqm/T5/FAM/Q:
5'-FAM-TGGTAGACAGGATGTTCCTAAGGTGTC-QSY-3'

TQMIC/hdv/F1:
5-gtggggacgccatctattc-3

TQMIC/hdv/R1:
5-tatgcgcgaggcatattcta-3

TQMIC/T1/JUN/Q:
5-CY5-CAGATACCGGTGCGCTGCGT-QSY-3

Amplification mixture C

HPV35/tqm4/F:
TCATGCAGGCAGTTCTAGGC

HPV35/tqm4/R:
GAAATCCAAACTTATTAGGATCTGGT

HPV35Tqm/T3/ABY/Q:
5'-ABY-AGCAGTACCCAAGGTATCTGGTTTGCA-QSY-3'

HPV39/tqm4/F:
ATGCTGGCAGCTCTAGATTATT

HPV39/tqm4/R:
TTAGGATCGGGCAATGTCAC

HPV39Tqm/T2/ABY/Q:
5'-ABY-TGAATGGTGGTCGCAAGCAGG-QSY-3'

HPV45/tqm4/F:
GCAGGCAGTTCCCGATTATT

HPV45/tqm4/R:
TCCAAATTTATTAGGATCGGGTAAA

HPV45Tqm/T1/VIC/Q
5'-VIC-CAG GCT GTT CCT AAG GTA TCC GCA-QSY-3'

HPV51/tqm4/F:
TGCAGGCAGTTCCAGACTAA

HPV51/tqm4/R:
GAGTCCAAACTTGTTAGGATCTGGT

HPV51Tqm/T1/ABY/Q:
5'-ABY-CCTCAACGCGTGCTGCTATTCC-QSY-3'

HPV66/tqm4/F2:
TGCAGGTAGCTCTAGGTTGCT

HPV66/tqm4/R:
TAGGATCAGGCAACCGTACC

HPV66Tqm/T1/FAM/Q:
5'-FAM-CAAATCTGGTACCAAAACAAACATCCC-QSY-3'

HPV68/tqm4/F:
TGCTGGTACATCTAGGTTATTAACTG

HPV68/tqm4/R:
CAGGAACACTAAATTTATTAGGATCAGG

HPV68Tqm//T2/FAM/Q:
5'-FAM-CTATGTCTGGGGGCCGCAAG-QSY-3'

TQMIC/hdv/F1:
5-gtggggacgccatctattc-3

TQMIC/hdv/R1:
5-tatgcgcgaggcatattcta-3

TQMIC/T1/JUN/Q:
5-CY5-CAGATACCGGTGCGCTGCGT-QSY-3

Amplification mixture D

FV/F1:
5'-TCTGAAAGGTTACTTCAAGGACAA-3'

FV/R1:
5'-CATCGCCTCTGGGCTAATAG-3'

FV/P4
5'-FAM-ctgtaagagcagatccctggacaggc-QSY-3'

TQMIC/hdv/F1:
5-gtggggacgccatctattc-3

TQMIC/hdv/R1:
5-tatgcgcgaggcatattcta-3

TQMIC/T1/JUN/Q:
5-CY5-CAGATACCGGTGCGCTGCGT-QSY-3

The present invention also provides an amplification mixture for the use in the detection of HPV, said amplification mixture comprising
(a) SEQ. ID No's: 1-3; and optionally SEQ. ID No's: 7-9
(b) SEQ. ID No's: 3-6; and optionally SEQ. ID No's: 7-9
(c) SEQ. ID No's: 10-12; and optionally SEQ. ID No's: 28-30
(d) SEQ. ID No's: 13-15; and optionally SEQ. ID No's: 28-30
(e) SEQ. ID No's: 16-18; and optionally SEQ. ID No's: 28-30
(f) SEQ. ID No's: 19-21; and optionally SEQ. ID No's: 28-30
(g) SEQ. ID No's: 22-24; and optionally SEQ. ID No's: 28-30
(h) SEQ. ID No's: 25-27; and optionally SEQ. ID No's: 28-30
(i) SEQ. ID No's: 31-33; and optionally SEQ. ID No's: 49-51
(j) SEQ. ID No's: 34-36; and optionally SEQ. ID No's: 49-51
(k) SEQ. ID No's: 37-39; and optionally SEQ. ID No's: 49-51
(l) SEQ. ID No's: 40-42; and optionally SEQ. ID No's: 49-51
(m) SEQ. ID No's: 43-45; and optionally SEQ. ID No's: 49-51
(n) SEQ. ID No's: 46-48; and optionally SEQ. ID No's: 49-51

Wherein SEQ ID Nos: 3, 6, 9, 12, 15, 18, 21, 24, 27, 30, 33, 36, 39, 42, 45, 48 and 51 are labelled with a quencher and dye, one at the 5' end and one at the 3' end. Preferably, SEQ ID Nos: 3, 6, 9, 12, 15, 18, 21, 24, 27, 30, 33, 36, 39, 42, 45, 48 and 51 are labelled with a dye at the 5' end and a quencher at the 3' end.

The present invention also provides an amplification mixture for the use in the detection of HPV, said amplification mixture comprising (a) SEQ. ID No's: 1-6; and optionally SEQ. ID No's: 7-9 or
(b) SEQ. ID No's: 10-27; and optionally SEQ. ID No's: 28-30 or
(c) SEQ. ID No's: 31-48; and optionally SEQ. ID No's: 49-51

Wherein SEQ ID Nos: 3, 6, 9, 12, 15, 18, 21, 24, 27, 30, 33, 36, 39, 42, 45, 48 and 51 are labelled with a quencher and dye, one at the 5' end and one at the 3' end. Preferably, SEQ ID Nos: 3, 6, 9, 12, 15, 18, 21, 24, 27, 30, 33, 36, 39, 42, 45, 48 and 51 are labelled with a dye at the 5' end and a quencher at the 3' end.

The present application also provides a kit for the use in the detection of HPV comprising one or more amplification mixtures selected from
(a) SEQ. ID No's: 1-3; and optionally SEQ. ID No's: 7-9
(b) SEQ. ID No's: 3-6; and optionally SEQ. ID No's: 7-9
(c) SEQ. ID No's: 10-12; and optionally SEQ. ID No's: 28-30
(d) SEQ. ID No's: 13-15; and optionally SEQ. ID No's: 28-30
(e) SEQ. ID No's: 16-18; and optionally SEQ. ID No's: 28-30
(f) SEQ. ID No's: 19-21; and optionally SEQ. ID No's: 28-30
(g) SEQ. ID No's: 22-24; and optionally SEQ. ID No's: 28-30
(h) SEQ. ID No's: 25-27; and optionally SEQ. ID No's: 28-30
(i) SEQ. ID No's: 31-33; and optionally SEQ. ID No's: 49-51
(j) SEQ. ID No's: 34-36; and optionally SEQ. ID No's: 49-51
(k) SEQ. ID No's: 37-39; and optionally SEQ. ID No's: 49-51
(l) SEQ. ID No's: 40-42; and optionally SEQ. ID No's: 49-51
(m) SEQ. ID No's: 43-45; and optionally SEQ. ID No's: 49-51
(n) SEQ. ID No's: 46-48; and optionally SEQ. ID No's: 49-51

Wherein SEQ ID Nos: 3, 6, 9, 12, 15, 18, 21, 24, 27, 30, 33, 36, 39, 42, 45, 48 and 51 are labelled with a quencher and dye, one at the 5' end and one at the 3' end. Preferably SEQ ID Nos: 3, 6, 9, 12, 15, 18, 21, 24, 27, 30, 33, 36, 39, 42, 45, 48 and 51 are labelled with a dye at the 5' end and a quencher at the 3' end The present application also provides a kit for for the use in the detection of HPV comprising one or more amplification mixtures selected from
(a) SEQ. ID No's: 1-6; and optionally SEQ. ID No's: 7-9 or
(b) SEQ. ID No's: 10-27; and optionally SEQ. ID No's: 28-30 or
(c) SEQ. ID No's: 31-48; and optionally SEQ. ID No's: 49-51

Wherein SEQ ID Nos: 3, 6, 9, 12, 15, 18, 21, 24, 27, 30, 33, 36, 39, 42, 45, 48 and 51 are labelled with a quencher and dye, one at the 5' end and one at the 3' end. Preferably, SEQ ID Nos: 3, 6, 9, 12, 15, 18, 21, 24, 27, 30, 33, 36, 39, 42, 45, 48 and 51 are labelled with a dye at the 5' end and a quencher at the 3' end.

Preferably the kit further comprises an amplification mixture comprising
(d) SEQ. ID Nos: 52-54 and optionally SEQ. ID Nos 55-57, Wherein SEQ ID Nos: 54 and 57 are labelled with a quencher and dye, one at the 5' end and one at the 3' end. Preferably, SEQ ID Nos: 54 and 57 are labelled with a dye at the 5' end and a quencher at the 3' end.

The kit can also include a package label or package insert having instructions thereon for using the mixture(s) of primers and pair(s) of probes to detect the presence or absence of human papillomavirus in a biological sample.

The kits can further comprise other components, such as reagents required for PCR. Such reagents include buffers, a suitable DNA polymerase, and dNTPs such as dATP, dCTP, dGTP and dTTP. The kit components can be presented in a number of vials or other containers. The reagents may be lyophilised for later reconstitution prior to use. Alternatively the components can be provided in suitable buffered solutions ready for use. Such solutions may contain suitable preservatives.

The invention will now be described with reference to the following non-limiting example:

EXAMPLE 2,522 low risk women aged 18-65 (low risk means no known HPV infection or cytological positivity 24 months prior to enrolment) were tested.

DNA extraction was carried out by a standard method utilizing centrifugation based using 96-well silica binding plates. This is a low cost and high throughput method.

PCR setup was carried out in 384-well format using liquid handling robots.

6 ul amplification mixture as detailed in the table below was added to 10 ul eluted DNA into each reaction

| Primer/Probe name | Quantity/ reaction | Starting concentration | Final concentration |
|---|---|---|---|
| Amplification mixture A | | | |
| HPV 16 tqm4 F 2x | 0.125 | 100 µM | 1 µM |
| HPV 16 tqm4 R 2x | 0.125 | 100 µM | 1 µM |
| HPV 16 TQM T1/VIC 2x | 0.025 | 100 µM | 0.2 µM |
| HPV 18 tqm4 F 2x | 0.125 | 100 µM | 1 µM |
| HPV 18 tqm4 R 2x | 0.125 | 100 µM | 1 µM |
| HPV 18 TQM T2/FAM 2x | 0.025 | 100 µM | 0.2 µM |
| IC2 hdv/F | 0.0625 | 100 µM | 0.5 µM |
| IC2 hdv/R | 0.0625 | 100 µM | 0.5 µM |
| IC T1 Cy5 | 0.0125 | 100 µM | 0.1 µM |
| D.V. | 1.6625 | — | — |
| Amplification mixture B | | | |
| HPV 31 tqm4 F | 0.0625 | 100 µM | 0.5 µM |
| HPV 31 tqm4 R | 0.0625 | 100 µM | 0.5 µM |
| HPV 31 TQM T2/VIC | 0.0125 | 100 µM | 0.1 µM |
| HPV 33 tqm4 F | 0.0625 | 100 µM | 0.5 µM |
| HPV 33 tqm4 R | 0.0625 | 100 µM | 0.5 µM |
| HPV 33 TQM T1/ABY | 0.0125 | 100 µM | 0.1 µM |
| HPV 52 tqm4 F | 0.0625 | 100 µM | 0.5 µM |
| HPV 52 tqm4 R | 0.0625 | 100 µM | 0.5 µM |
| HPV 52 TQM T1/ABY !!! | 0.0125 | 100 µM | 0.1 µM |
| HPV 56 tqm4 F 2x | 0.125 | 100 µM | 1 µM |
| HPV 56 tqm4 R 2x | 0.125 | 100 µM | 1 µM |
| HPV 56 TQM T2/ABY 2x | 0.025 | 100 µM | 0.2 µM |
| HPV 58 tqm4 F | 0.0625 | 100 µM | 0.5 µM |
| HPV 58 tqm4 R | 0.0625 | 100 µM | 0.5 µM |
| HPV 58 TQM T1/FAM | 0.0125 | 100 µM | 0.1 µM |
| HPV 59 tqm4 F | 0.0625 | 100 µM | 0.5 µM |
| HPV 59 tqm4 R | 0.0625 | 100 µM | 0.5 µM |
| HPV 59 TQM T5/FAM | 0.0125 | 100 µM | 0.1 µM |
| IC2 hdv/F | 0.0625 | 100 µM | 0.5 µM |
| IC2 hdv/R | 0.0625 | 100 µM | 0.5 µM |
| IC T1 Cy5 | 0.0125 | 100 µM | 0.1 µM |
| D.V. | 1.3 | — | — |

| Primer/Probe name | Quantity/ reaction | Starting concentration | Final concentration |
|---|---|---|---|
| Amplification mixture C | | | |
| HPV 35 tqm4 F | 0.0625 | 100 μM | 0.5 μM |
| HPV 35 tqm4 R | 0.0625 | 100 μM | 0.5 μM |
| HPV 35 TQM T3/ABY !!! | 0.0125 | 100 μM | 0.1 μM |
| HPV 39 tqm4 F | 0.0625 | 100 μM | 0.5 μM |
| HPV 39 tqm4 R | 0.0625 | 100 μM | 0.5 μM |
| HPV 39 TQM T2/ABY !!! | 0.0125 | 100 μM | 0.1 μM |
| HPV 45 tqm4 F | 0.0625 | 100 μM | 0.5 μM |
| HPV 45 tqm4 R | 0.0625 | 100 μM | 0.5 μM |
| HPV 45 TQM T1/VIC | 0.0125 | 100 μM | 0.1 μM |
| HPV 51 tqm4 F | 0.0625 | 100 μM | 0.5 μM |
| HPV 51 tqm4 R | 0.0625 | 100 μM | 0.5 μM |
| HPV 51 TQM T1/ABY | 0.0125 | 100 μM | 0.1 μM |
| HPV 66 tqm4 F | 0.0625 | 100 μM | 0.5 μM |
| HPV 66 tqm4 R | 0.0625 | 100 μM | 0.5 μM |
| HPV 66 TQM T1/FAM | 0.0125 | 100 μM | 0.1 μM |
| HPV 68 tqm4 F | 0.0625 | 100 μM | 0.5 μM |
| HPV 68 tqm4 R | 0.0625 | 100 μM | 0.5 μM |
| HPV 68 TQM T2/FAM | 0.0125 | 100 μM | 0.1 μM |
| IC2 hdv/F | 0.0625 | 100 μM | 0.5 μM |
| IC2 hdv/R | 0.0625 | 100 μM | 0.5 μM |
| IC T1 Cy5 | 0.0125 | 100 μM | 0.1 μM |
| D.V. | 1.4375 | — | — |
| Amplification mixture D | | | |
| FV F1 | 0.0625 | 100 μM | 0.5 μM |
| FV R1 | 0.0625 | 100 μM | 0.5 μM |
| FV PN4/FAM | 0.0125 | 100 μM | 0.1 μM |
| IC2 hdv/F | 0.0625 | 100 μM | 0.5 μM |
| IC2 hdv/R | 0.0625 | 100 μM | 0.5 μM |
| IC T1 Cy5 | 0.0125 | 100 μM | 0.1 μM |
| D.V. | 2.175 | — | — |

TAQman PCR was carried out using standard Taqman thermal profile as shown

| | Temperature (° C.) | Time (sec) | Number of cycles |
|---|---|---|---|
| Denaturing | 95 | 140 | 1 |
| Denaturing | 95 | 1 | 45 |
| Annealing | 60 | 30 | |

The results obtained were compared to those obtained using the Roche COBAS method. Roche COBAS HPV found 20.22% of samples positive (with 95% confidence interval: 18.67% to 21.84%)

The method of the present invention identified 24.23% samples as positive (95% confidence interval: 22.57% to 25.95%)

The method of the present invention found significantly more positive samples and thus identified more women who are at risk of developing lesions and cancerous conditions.

The invention claimed is:

1. A method for detecting the presence of HPV, comprising amplifying a nucleic acid obtained from a sample utilizing one or more amplification mixtures, wherein the amplification mixtures are selected from:

(a) Amplification mixture 1 comprising
  5'-TCATGCAGGAACATCCAGACT-3' (SEQ. ID NO: 1)
  5'-CCAAACTTATTGGGGTCAGG-3' (SEQ. ID NO: 2)
  5'-TTGCAGTTGGACATCCCTATTTTCC-3' (SEQ. ID NO: 3)

(b) Amplification mixture 2 comprising
  5'-TCATGCTGGCAGCTCTAGATT-3' (SEQ. ID NO: 4)
  5'-GGTCAGGTAACTGCACCCTAAA-3' (SEQ. ID NO: 5)
  5'-AGGGTTCCTGCAGGTGGTGGC-3' (SEQ. ID NO: 6)

(c) Amplification mixture 3 comprising
  5'-CACGCAGGCAGTGCTAGG-3' (SEQ. ID NO: 10)
  5'-TCCAAATTTGTTTGGATCTGG-3' (SEQ. ID NO: 11)
  5'-CAGTAGGCCATCCATATTATTCCATACC-3' (SEQ. ID NO: 12)

(d) Amplification mixture 4 comprising
  5'-GCTGGTAGTTCCAGACTTCTTGC-3' (SEQ. ID NO: 13)
  5'-CCAAATTTATTAGGATCTGGTAAACG-3' (SEQ. ID NO: 14)
  5'-TGGTACCCAAAGTATCAGGCTTGCA-3' (SEQ. ID NO: 15)

(e) Amplification mixture 5 comprising
  5'-TTATGCAGGCAGTTCTCGATT-3' (SEQ. ID NO: 16)
  5'-GGGTCCGGCAATTTAATTCT-3' (SEQ. ID NO: 17)
  5'-AGGACATCCCTATTTTTCTATTAAAAACACCAGT-3' (SEQ. ID NO: 18)

(f) Amplification mixture 6 comprising
  5'-TATCATGCAGGCAGTTCACG-3' (SEQ. ID NO: 19)
  5'-AAACTTATTAGGGTCGGGCAAC-3' (SEQ. ID NO: 20)
  5'-GGACAATACCAAAACAAACATTCCCA-3' (SEQ. ID NO: 21)

(g) Amplification mixture 7 comprising
  5'-TGCTGGCAGTTCCAGACTTT-3' (SEQ. ID NO: 22)
  5'-AAACCAAATTTATTGGGATCAGG-3' (SEQ. ID NO: 23)
  5'-TCCCAAGGTATCAGGCTTACAGTATAGGG-3' (SEQ. ID NO: 24)

(h) Amplification mixture 8 comprising
  5'-ACGCAGGCAGTTCCAGACT-3' (SEQ. ID NO: 25)
  5'-GGCCAAATTTATTGGGATCA-3' (SEQ. ID NO: 26)
  5'-TGGTAGACAGGATGTTCCTAAGGTGTC-3' (SEQ. ID NO: 27);
or (i) Amplification mixture 9 comprising
  5'-TCATGCAGGCAGTTCTAGGC-3' (SEQ. ID NO: 31)
  5'-GAAATCCAAACTTATTAGGATCTGGT-3' (SEQ. ID NO: 32)
  5'-AGCAGTACCCAAGGTATCTGGTTTGCA-3' (SEQ. ID NO: 33)

(j) Amplification mixture 10 comprising
  5'-ATGCTGGCAGCTCTAGATTATT-3' (SEQ. ID NO: 34)
  5'-TTAGGATCGGGCAATGTCAC-3' (SEQ. ID NO: 35)
  5'-TGAATGGTGGTCGCAAGCAGG-3' (SEQ. ID NO: 36)

(k) Amplification mixture 11 comprising
  5'-GCAGGCAGTTCCCGATTATT-3' (SEQ. ID NO: 37)
  5'-TCCAAATTTATTAGGATCGGGTAAA-3' (SEQ. ID NO: 38)
  5'-CAG GCT GTT CCT AAG GTA TCC GCA-3' (SEQ. ID NO: 39)

(l) Amplification mixture 12 comprising
  5'-TGCAGGCAGTTCCAGACTAA-3' (SEQ. ID NO: 40)
  5'-GAGTCCAAACTTGTTAGGATCTGGT-3' (SEQ. ID NO: 41)
  (SEQ. ID NO: 42)

-continued
```
5'-CCTCAACGCGTGCTGCTATTCC-3'
```

(m) Amplification mixture 13 comprising
```
                            (SEQ. ID NO: 43)
5'-TGCAGGTAGCTCTAGGTTGCT-3'

(SEQ. ID NO: 44)
5'-TAGGATCAGGCAACCGTACC-3'

(SEQ. ID NO: 45)
CAAATCTGGTACCAAAACAAACATCCC-3'
```

(n) Amplification mixture 14 comprising
```
                            (SEQ. ID NO: 46)
TGCTGGTACATCTAGGTTATTAACTG-3'

(SEQ. ID NO: 47)
5'-CAGGAACACTAAATTTATTAGGATCAGG-3'

(SEQ. ID NO: 48)
5'-CTATGTCTGGGGCCGCAAG.-3';
```

Wherein SEQ ID No's: 3, 6, 12, 15, 18, 21, 24, 27, 33, 36, 39, 42, 45 and 48 are labelled with a quencher and dye, one at the 5' end and one at the 3' end.

2. A method for detecting the presence of HPV, comprising amplifying a nucleic acid obtained from a sample utilizing one or more amplification mixtures, wherein the amplification mixtures are selected from:

(a) Amplification mixture 15 comprising
```
                            (SEQ. ID NO: 1)
5'-TCATGCAGGAACATCCAGACT-3'

(SEQ. ID NO: 2)
5'-CCAAACTTATTGGGGTCAGG-3'

(SEQ. ID NO: 3)
5'-TTGCAGTTGGACATCCCTATTTTCC-3'

(SEQ. ID NO: 4)
5'-TCATGCTGGCAGCTCTAGATT-3'

(SEQ. ID NO: 5)
5'-GGTCAGGTAACTGCACCCTAAA-3'

(SEQ. ID NO: 6)
5'-AGGGTTCCTGCAGGTGGTGGC-3'
```

(b) Amplification mixture 16 comprising
```
                            (SEQ. ID NO: 10)
5'-CACGCAGGCAGTGCTAGG-3'

(SEQ. ID NO: 11)
5'-TCCAAATTTGTTTGGATCTGG-3'

(SEQ. ID NO: 12)
5'-CAGTAGGCCATCCATATTATTCCATACC-3'

(SEQ. ID NO: 13)
5'-GCTGGTAGTTCCAGACTTCTTGC-3'

(SEQ. ID NO: 14)
5'-CCAAATTTATTAGGATCTGGTAAACG-3'

(SEQ. ID NO: 15)
5'-TGGTACCCAAAGTATCAGGCTTGCA-3'

(SEQ. ID NO: 16)
5'-TTATGCAGGCAGTTCTCGATT-3'

(SEQ. ID NO: 17)
5'-GGGTCCGGCAATTTAATTCT-3'

(SEQ. ID NO: 18)
5'-AGGACATCCCTATTTTTCTATTAAAAACACCAGT-3'

(SEQ. ID NO: 19)
5'-TATCATGCAGGCAGTTCACG-3'

(SEQ. ID NO: 20)
5'-AAACTTATTAGGGTCGGGCAAC-3'

(SEQ. ID NO: 21)
5'-GGACAATACCAAAACAAACATTCCCA-3'

(SEQ. ID NO: 22)
5'-TGCTGGCAGTTCCAGACTTT-3'

(SEQ. ID NO: 23)
5'-AAACCAAATTTATTGGGATCAGG-3'

(SEQ. ID NO: 24)
5'-TCCCAAGGTATCAGGCTTACAGTATAGGG-3'

(SEQ. ID NO: 25)
5'-ACGCAGGCAGTTCCAGACT-3'

(SEQ. ID NO: 26)
5'-GGCCAAATTTATTGGGATCA-3'

(SEQ. ID NO: 27)
5'-TGGTAGACAGGATGTTCCTAAGGTGTC-3';
or
```

(c) Amplification mixture 17 comprising
```
                            (SEQ. ID NO: 31)
5'-TCATGCAGGCAGTTCTAGGC-3'

(SEQ. ID NO: 32)
5'-GAAATCCAAACTTATTAGGATCTGGT-3'

(SEQ. ID NO: 33)
5'-AGCAGTACCCAAGGTATCTGGTTTGCA-3'

(SEQ. ID NO: 34)
5'-ATGCTGGCAGCTCTAGATTATT-3'

(SEQ. ID NO: 35)
5'-TTAGGATCGGGCAATGTCAC-3'

(SEQ. ID NO: 36)
5'-TGAATGGTGGTCGCAAGCAGG-3'

(SEQ. ID NO: 37)
5'-GCAGGCAGTTCCCGATTATT-3'

(SEQ. ID NO: 38)
5'-TCCAAATTTATTAGGATCGGGTAAA-3'

(SEQ. ID NO: 39)
5'-CAG GCT GTT CCT AAG GTA TCC GCA-3'

(SEQ. ID NO: 40)
5'-TGCAGGCAGTTCCAGACTAA-3'

(SEQ. ID NO: 41)
5'-GAGTCCAAACTTGTTAGGATCTGGT-3'

(SEQ. ID NO: 42)
5'-CCTCAACGCGTGCTGCTATTCC-3'

(SEQ. ID NO: 43)
5'-TGCAGGTAGCTCTAGGTTGCT-3'

(SEQ. ID NO: 44)
5'-TAGGATCAGGCAACCGTACC-3'

(SEQ. ID NO: 45)
CAAATCTGGTACCAAAACAAACATCCC-3'

(SEQ. ID NO: 46)
TGCTGGTACATCTAGGTTATTAACTG-3'
```

-continued

```
                                     (SEQ. ID NO: 47)
5'-CAGGAACACTAAATTTATTAGGATCAGG-3'

(SEQ. ID NO: 48)
5'-CTATGTCTGGGGGCCGCAAG.-3';
```

Wherein SEQ ID No's: 3, 6, 12, 15, 18, 21, 24, 27, 33, 36, 39, 42, 45 and 48 are labelled with a quencher and dye, one at the 5' end and one at the 3' end.

3. The method of claim 1, further comprising amplifying the nucleic acid obtained from a sample with an amplification mixture capable of amplifying a human control gene.

4. The method of claim 3 wherein the human control gene is factor V leiden gene.

5. The method of claim 3 wherein the amplification mixture capable of amplifying a human control gene is

```
    Amplification mixture 18 comprising
                                     (SEQ. ID NO: 52)
5'-TCTGAAAGGTTACTTCAAGGACAA-3'

(SEQ. ID NO: 53)
5'-CATCGCCTCTGGGCTAATAG-3'

(SEQ. ID NO: 54)
5'-CTGTAAGAGCAGATCCCTGGACAGGC-3'
```

Wherein SEQ ID No's: 54 is labelled with a quencher and dye, one at the 5' end and one at the 3' end.

6. The method of claim 1 wherein the amplification mixture further comprises one or more internal control primers.

7. The method of claim 6 wherein the amplification mixture further comprises

```
                                     (SEQ. ID NO: 7)
5'-GTGGGGACGCCATCTATTC-3'

(SEQ. ID NO: 8)
5'-TATGCGCGAGGCATATTCTA-3'
and (SEQ. ID NO: 9)
5'-CAGATACCGGTGCGCTGCGT-3';.
```

8. The method of claim 2 wherein
(a) Amplification mixture 15 further comprises:

```
(a) Amplification mixture 15 further comprises:
                                     (SEQ. ID NO: 7)
5'-GTGGGGACGCCATCTATTC-3'

(SEQ. ID NO: 8)
5'-TATGCGCGAGGCATATTCTA-3'

(SEQ. ID NO: 9)
5'-CAGATACCGGTGCGCTGCGT-3';;
and/or (b) Amplification mixture 16 further comprises
                                     (SEQ. ID NO: 28)
5'-GTGGGGACGCCATCTATTC-3

(SEQ. ID NO: 29)
5'-TATGCGCGAGGCATATTCTA-3

(SEQ. ID NO: 30)
5'-CAGATACCGGTGCGCTGCGT-3';;
and/or
```

```
(c) Amplification mixture 17 further comprises
                                     (SEQ. ID NO: 49)
5'-GTGGGGACGCCATCTATTC-3'

(SEQ. ID NO: 50)
5'-TATGCGCGAGGCATATTCTA-3'

(SEQ. ID NO: 51)
5'-CAGATACCGGTGCGCTGCGT-3';
and/or (d) Amplification mixture 18 further comprises
                                     (SEQ. ID NO: 55)
5'-GTGGGGACGCCATCTATTC-3

(SEQ. ID NO: 56)
5'-TATGCGCGAGGCATATTCTA-3'

(SEQ. ID NO: 57)
5'-CAGATACCGGTGCGCTGCGT-3'
```

Wherein SEQ ID No's: 9, 30, 51 and 57 are labelled with a quencher and dye, one at the 5' end and one at the 3' end.

9. The method of claim 2 wherein
a) Amplification mixture 15 consists of SEQ. ID No's: 1-6; and/or
b) Amplification mixture 16 consists of SEQ. ID No's: 10-27; and/or
c) Amplification mixture 17 consists of SEQ. ID No's: 31-48; and/or
d) Amplification mixture 18 consists of SEQ. ID No's: 52-54.

10. The method of claim 1 utilizing two or more amplification mixtures, where the amplification reaction for each amplification mixture is carried out concurrently or sequentially.

11. The method of claim 1 wherein said nucleic acid is amplified utilizing PCR.

12. The method of claim 11 wherein said method utilizes real-time PCR.

13. The method of claim 1 wherein said nucleic acid is amplified utilizing Taqman system.

14. The method of claim 1 wherein said quencher is QSY and said dye is selected from VIC, ABY, VIC, FAM or JUN.

15. The method of claim 1 wherein the sample is a cell sample.

16. The method of claim 15 wherein the sample is a Pap smear sample.

17. An amplification mixture for the use in the detection of HPV, said amplification mixture comprising
(a) SEQ. ID No's: 1-3; and optionally SEQ. ID No's: 7-9
(b) SEQ. ID No's: 3-6; and optionally SEQ. ID No's: 7-9
(c) SEQ. ID No's: 10-12; and optionally SEQ. ID No's: 28-30
(d) SEQ. ID No's: 13-15; and optionally SEQ. ID No's: 28-30
(e) SEQ. ID No's: 16-18; and optionally SEQ. ID No's: 28-30
(f) SEQ. ID No's: 19-21; and optionally SEQ. ID No's: 28-30
(g) SEQ. ID No's: 22-24; and optionally SEQ. ID No's: 28-30
(h) SEQ. ID No's: 25-27; and optionally SEQ. ID No's: 28-30
(i) SEQ. ID No's: 31-33; and optionally SEQ. ID No's: 49-51
(j) SEQ. ID No's: 34-36; and optionally SEQ. ID No's: 49-51
(k) SEQ. ID No's: 37-39; and optionally SEQ. ID No's: 49-51

(l) SEQ. ID No's: 40-42; and optionally SEQ. ID No's: 49-51
(m) SEQ. ID No's: 43-45; and optionally SEQ. ID No's: 49-51
(n) SEQ. ID No's: 46-48; and optionally SEQ. ID No's: 49-51

Wherein SEQ ID No's: 3, 6, 9, 12, 15, 18, 21, 24, 27, 30, 33, 36, 39, 42, 45, 48 and 51 are labelled with a quencher and dye, one at the 5' end and one at the 3' end.

18. The amplification mixture for the use of claim 17, said amplification mixture comprising
    (a) SEQ. ID No's: 1-6; and optionally SEQ. ID No's: 7-9 or
    (b) SEQ. ID No's: 10-27; and optionally SEQ. ID No's: 28-30 or
    (c) SEQ. ID No's: 31-48; and optionally SEQ. ID No's: 49-51

Wherein SEQ ID No's: 3, 6, 9, 12, 15, 18, 21, 24, 27, 30, 33, 36, 39, 42, 45, 48 and 51 are labelled with a quencher and dye, one at the 5' end and one at the 3' end.

19. The method of claim 17 wherein SEQ ID Nos: 3, 6, 9, 12, 15, 18, 21, 24, 27, 30, 33, 36, 39, 42, 45, 48 and 51 are labelled with a dye at the 5' end and a quencher at the 3' end.

20. The method of claim 1 wherein the amplification reaction for each amplification mixture is carried out in a separate vessel.

21. The method of claim 1 wherein up to three amplification mixtures, optionally together with one or more internal control primers and/or an amplification mixture capable of amplifying a human control gene are used in a single reaction carried out in one vessel.

22. A kit for the use in the detection of HPV comprising one or more amplification mixtures selected from
    a) SEQ. ID No's: 1-3; and optionally SEQ. ID No's: 7-9
    (b) SEQ. ID No's: 3-6; and optionally SEQ. ID No's: 7-9
    (c) SEQ. ID No's: 10-12; and optionally SEQ. ID No's: 28-30
    (d) SEQ. ID No's: 13-15; and optionally SEQ. ID No's: 28-30
    (e) SEQ. ID No's: 16-18; and optionally SEQ. ID No's: 28-30
    (f) SEQ. ID No's: 19-21; and optionally SEQ. ID No's: 28-30
    (g) SEQ. ID No's: 22-24; and optionally SEQ. ID No's: 28-30
    (h) SEQ. ID No's: 25-27; and optionally SEQ. ID No's: 28-30
    (i) SEQ. ID No's: 31-33; and optionally SEQ. ID No's: 49-51
    (j) SEQ. ID No's: 34-36; and optionally SEQ. ID No's: 49-51
    (k) SEQ. ID No's: 37-39; and optionally SEQ. ID No's: 49-51
    (l) SEQ. ID No's: 40-42; and optionally SEQ. ID No's: 49-51
    (m) SEQ. ID No's: 43-45; and optionally SEQ. ID No's: 49-51
    (n) SEQ. ID No's: 46-48; and optionally SEQ. ID No's: 49-51

Wherein SEQ ID No's: 3, 6, 9, 12, 15, 18, 21, 24, 27, 30, 33, 36, 39, 42, 45, 48 and 51 are labelled with a quencher and dye, one at the 5' end and one at the 3' end.

23. The kit for the use in the detection of HPV of claim 22 comprising one or more amplification mixtures selected from
    (a) SEQ. ID No's: 1-6; and optionally SEQ. ID No's: 7-9 or
    (b) SEQ. ID No's: 10-27; and optionally SEQ. ID No's: 28-30 or
    (c) SEQ. ID No's: 31-48; and optionally SEQ. ID No's: 49-51

Wherein SEQ ID No's: 3, 6, 9, 12, 15, 18, 21, 24, 27, 30, 33, 36, 39, 42, 45, 48 and 51 are labelled with a quencher and dye, one at the 5' end and one at the 3' end.

24. The kit of claim 22 further comprising an amplification mixture comprising
    (d) SEQ. ID No's: 52-54 and optionally SEQ. ID No's 55-57, Wherein SEQ ID No's: 54 and 57 are labelled with a quencher and dye, one at the 5' end and one at the 3' end.

* * * * *